United States Patent

Mohr et al.

[11] Patent Number: 5,492,641
[45] Date of Patent: Feb. 20, 1996

[54] β-AMINONITRILES AND N-ALKYL-1,3-PROPYLENEDIAMINES AND THEIR USE AS FUEL ADDITIVES AND LUBRICANT ADDITIVES

[75] Inventors: Juergen Mohr, Gruenstadt; Knut Oppenlaender, Ludwigshafen; Lothar Franz, Mutterstadt; Juergen Thomas, Fussgoenheim, all of Germany

[73] Assignee: BASF Aktiengesellschaft, Ludwigshafen, Germany

[21] Appl. No.: 347,213

[22] Filed: Nov. 21, 1994

Related U.S. Application Data

[63] Continuation of Ser. No. 54,066, Apr. 29, 1993, abandoned.

[30] Foreign Application Priority Data

May 4, 1992 [DE] Germany .................. 42 14 810.3

[51] Int. Cl.[6] ................................................ C10M 133/24
[52] U.S. Cl. .............................. 252/50; 558/408; 558/452
[58] Field of Search ................................ 558/452, 408; 252/50; 44/384, 412; C10M 133/24

[56] References Cited

U.S. PATENT DOCUMENTS

| | | | |
|---|---|---|---|
| 2,898,295 | 8/1959 | MacKenzie | 252/28 |
| 3,244,491 | 4/1966 | Marsh et al. | 44/384 |
| 3,398,196 | 8/1968 | Miller et al. | 564/511 |
| 3,438,757 | 4/1969 | Honnen et al. | |
| 3,565,804 | 2/1971 | Honnen et al. | |
| 3,774,313 | 11/1973 | Occhialini et al. | |
| 4,031,015 | 6/1977 | Miller | 252/50 |
| 4,058,469 | 11/1977 | Hoke | 252/51.5 R |
| 4,209,408 | 6/1980 | Hoke | 252/47 |
| 4,332,595 | 6/1982 | Herbstman et al. | |

FOREIGN PATENT DOCUMENTS

| | | |
|---|---|---|
| 2805822 | 8/1979 | Germany . |
| 1405652 | 9/1975 | United Kingdom . |

*Primary Examiner*—Prince Willis, Jr.
*Assistant Examiner*—Cephia D. Toomer
*Attorney, Agent, or Firm*—Keil & Weinkauf

[57] ABSTRACT

β-Aminonitriles of the following formula I

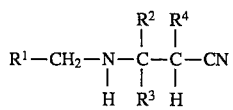

where $R^1$ is an aliphatic hydrocarbon radical having alkyl side groups and a number average molecular weight of from 250 to 5,000 and $R^2$, $R^3$ and $R^4$, independently of one another, are each hydrogen or $C_1$–$C_8$-alkyl and $R^2$ or $R^4$ is also phenyl, and alkylpropylenediamines prepared from the β-aminonitriles by hydrogenation are used as additives in fuels and lubricants.

5 Claims, No Drawings

β-AMINONITRILES AND N-ALKYL-1,3-PROPYLENEDIAMINES AND THEIR USE AS FUEL ADDITIVES AND LUBRICANT ADDITIVES

This application is a continuation of application Ser. No. 08/054,066, filed on Apr. 29, 1993, now abandoned.

The present invention relates to β-aminonitriles which are substituted at the amine nitrogen by a long-chain alkyl radical, N-alkyl-1,3-propylenediamines which are obtained from the β-aminonitriles by hydrogenation, processes for the preparation of the β-aminonitriles and of the N-alkyl-1,3-propylenediamines, and fuels and lubricants which contain these compounds as additives.

Carburetor and intake system of gasoline engines as well as injection systems for fuel metering in gasoline and diesel engines are increasingly contaminated by impurities due to dust particles from the air, uncombusted hydrocarbon residues from the combustion chamber and the crankcase vent gases passed into the carburetor.

These residues shift the air/fuel ratio during idling and in the lower part-load range so that the mixture becomes richer and the combustion more incomplete and in turn the amounts of uncombusted or partly combusted hydrocarbons in the exhaust gas become greater and the gasoline consumption increases.

It is known that these disadvantages can be avoided by using fuel additives for keeping valves and carburetors and injection systems clean (cf. for example: M. Rossenbeck in Katalysatoren, Tenside, Mineralöladditive, Editors J. Falbe, U. Hasserodt, page 223 et seq., G. Thieme Verlag, Stuttgart 1973).

A distinction is made between two generations, depending on the mode of action as well as on the preferred site of action of such detergent additives.

The first generation of additives were able only to prevent the formation of deposits in the intake system but not to remove existing deposits, whereas the additives of the second generation can do both (keep-clean and clean-up effect), particularly because of their advantageous thermal oxidation properties in zones at relatively high temperatures, i.e. in the intake valves.

The molecular structural principle of these additives which act as detergents can be described generally as the linking of polar structures to generally relatively high molecular weight, nonpolar or oleophilic radicals.

Typical members of the second generation of additives are often products based on polyisobutenes in the nonpolar moiety. Among these in turn, additives of the polyisobutylamine type are particularly noteworthy.

Detergents of the polyisobutylene type are obtained starting from polyisobutenes, essentially by two processes.

The first process involves chlorination of the polymeric parent structure and subsequent nucleophilic substitution by amines or ammonia. Owing to the preparation (addition of $Cl_2$, substitution of a chlorine atom by the amine, elimination of HCl), these products have a double bond. The disadvantage of this process is in particular the use of chlorine and the occurrence of chlorine-containing and chloride-containing products, which are now not at all desirable and are as far as possible avoided (German Laid-Open Applications DOS 2,129,491 and DOS 2,245,918 and U.S. Pat. Nos. 3,565,804 and 3,438,757).

In the second process, a reactive polyisobutene is first hydroformylated in an oxo synthesis and then hydrogenated under aminating conditions in the presence of ammonia (German Laid-Open Application DOS 3,611,220).

The latter products generally have excellent efficiency in keeping valves and carburettors clean but are at most neutral in their effect on an engine lubricant, particularly with regard to their sludge dispersing effect.

U.S. Pat. No. 4,332,595 describes polyetheramines which are prepared via cyanoethylation and therefore likewise contain no chlorine. However, these polyetheramines have only a detergent effect and are generally poorly soluble in oils.

One problem which occurs in this connection is the effect on the lubricant of fuel additives which enter the lubricant circulation of an engine in a small amount but continuously via the combustion chamber.

Once they have entered the lubricant, such additives must on no account adversely affect its properties and function. The effect of the fuel additives is therefore also taken into account particularly with regard to the formation and dispersing of the oil sludge. However, most of the known detergents show neutral behavior with regard to oil sludge.

If a positive effect of a fuel additive or of the active ingredients present therein on the lubricant is also desired, it is then useful also to add dispersant substances to the fuel.

Substances which simultaneously combine the properties of both detergents and dispersants are ideal in this connection and are of particular industrial interest.

It is an object of the present invention to provide substances which are halogen-free and, as additives in fuels, have an oil sludge-dispersing effect in addition to their positive effect in the intake system of a gasoline engine.

We have found that this object is achieved both by β-aminonitriles of the following formula I

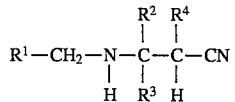

where $R^1$ is an aliphatic hydrocarbon radical having alkyl side groups and a number average molecular weight of from 250 to 5,000 and $R^2$, $R^3$ and $R^4$, independently of one another, are each hydrogen or $C_1$–$C_8$-alkyl or $R^2$ or $R^4$ is phenyl,
and by
N-alkyl-1,3-propylenediamines of the following formula II

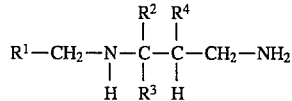

where $R^1$ to $R^4$ have the abovementioned meanings, which are obtained by hydrogenating the β-aminonitriles of the above formula I over a conventional hydrogenation catalyst under superatmospheric pressure at from 50° to 300° C. in the presence of $NH_3$.

It is found, surprisingly, that the novel derivatives of polyisobutylamines, in contrast to the amines on which they are based, not only have a valve-cleaning effect but also advantageously affect the sludge-carrying capacity of engine oils containing little or no additives. This effect is present to the same extent both in the case of the cyanoethylated members and in the aminopropylated members obtained by hydrogenation thereof.

The alkyl side groups in $R^1$ are preferably branched or straight-chain alkyl radicals of 1 to 30, in particular 1 to 4, carbon atoms.

Particularly preferred compounds are those in which $R^2$ and $R^3$ are each hydrogen and $R^4$ is hydrogen or methyl and/or $R^1$ is a polybutyl or polyisobutyl radical derived from isobutene and 0–30% by weight of n-butene.

Owing to their preparation, the novel substances contain no halogen and also have no unsaturated components.

This is achieved by virtue of the fact that the substances are prepared by a process which takes place without intermediate halogenation steps.

The present invention therefore also relates to a process for the preparation of β-aminonitriles of the above formula I, wherein an amine of the formula III

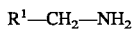

$$R^1-CH_2-NH_2 \qquad III$$

is reacted with a nitrile of the general formula IV

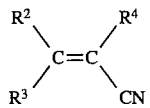

$$\begin{array}{c} R^2 \\ \diagdown \\ R^3 \end{array} C=C \begin{array}{c} R^4 \\ \diagdown \\ CN \end{array} \qquad IV$$

in the presence or absence of a catalyst, $R^1$ to $R^4$ having the abovementioned meanings.

The present invention furthermore relates to a process for the preparation of N-alkyl-1,3-propylenediamines of the above formula II, wherein the β-aminonitrile of the formula I is hydrogenated over a conventional hydrogenation catalyst under superatmospheric pressure at from 50° to 300° C. in the presence of $NH_3$.

The polyisobutylamines of the above formula III which are preferably used as starting materials are preferably obtained by hydroformylation and subsequent amination of polyisobutenes in a conventional manner.

The polyisobutene used for this purpose preferably has a molecular weight (Mn) of from 500 to 5,000, in particular from 800 to 1,500. It is obtained by cationic polymerization of isobutene by a known process, termination of the polymer chain in the monomer last incorporated leaving behind a double bond which can be used for the purpose of further functionalization (cf. for example German Laid-Open Application DOS 2,702,604).

The cyanoethylation of the polyisobutylamine is carried out in a conventional manner (cf. for example Kirk-Othmer, Encyclopedia of Chemical Technology, 3rd Ed., Vol. 7, pages 370–376, J. Wiley, 1979), for example by reacting the amine with acrylonitrile at from 50° to 120° C.

The catalytic hydrogenation of the resulting nitriles of the formula I to give the amines of the formula II is also carried out in a conventional manner, for example in an autoclave at superatmospheric pressure and at from 50° to 300° C., preferably from 80° to 150° C., in the presence of hydrogen and $NH_3$, over a conventional hydrogenation catalyst, e.g. Raney cobalt or Raney nickel.

Owing to their properties, the novel β-aminonitriles and/or N-alkyl-1,3-propylenediamines are used as detergents and dispersants in fuels, in particular in fuels for gasoline engines. However, they may also be used in lubricants.

If the β-aminonitriles and/or N-alkyl-1,3-propylenediamines are used in fuels, they are preferably added in an amount of from 10 to 5,000 ppm, in particular from 50 to 1,000 ppm. As a rule, larger amounts must be added to lubricants, and the amounts here may be from 0.1 to 6, in particular from 0.5 to 5%, by weight.

If it is intended primarily to make use of the dispersant properties of the novel substances, they may also be combined with conventional detergents as additional additives.

In principle, any known product among the products suitable for this purpose may be used as a detergent component in the mixture with the novel substances as dispersants, as described, for example, by J. Falbe and U. Hasserodt, Katalysatoren, Tenside und Mineralöladditive, G. Thieme Verlag Stuttgart, 1978, page 221 et seq. or by K. Owen, Gasoline and Diesel Fuel Additives, John Wiley & Sons 1989, page 23 et seq.

N-containing detergents, for example compounds which contain an amino or amido group, are preferably used. Polyisobutylamines according to European Patent 0,244,616, ethylenediaminetetraacetamides and/or -imides according to European Patent 0,188,786 or polyetheramines according to European Patent 0,356,725 are particularly suitable, reference being made to the definitions in these publications. The products described there also have the advantage of being chlorine-free or chloride-free, according to their preparation.

If it is intended primarily to make use of the detergent effect of the novel β-aminonitriles and/or N-alkyl-1,3-propylenediamines, these substances may also be combined with carrier oils. Such carrier oils are known; polyglycol-based carrier oils, for example corresponding ethers and/or esters, as described in U.S. Pat. No. 5,004,478 or DE 38 38 918 A1, are particularly suitable. Polyoxyalkylenemonools having terminal hydrocarbon groups (U.S. Pat. No. 4,877,416) or carrier oils as disclosed in DE 41 42 241.4 may also be used.

Suitable fuels for gasoline engines are leaded and in particular unleaded regular and premium grade gasoline. Gasoline may also contain components other than hydrocarbons, for example alcohols, such as methanol, ethanol or tert-butanol, and ethers, e.g. methyl tert-butyl ether. In addition to the alkoxylated polyetheramines to be used according to the invention, the fuels generally also contain further additives, such as corrosion inhibitors, stabilizers, antioxidants and/or further detergents.

Corrosion inhibitors are generally ammonium salts of organic carboxylic acids which tend to form films because the starting compounds have the appropriate structure. Amines for reducing the pH are also frequently present in corrosion inhibitors. Heterocyclic aromatics are generally used for corrosion protection of nonferrous metals.

The products are tested for suitability as fuel additives by means of engine tests:

The effect as a valve cleaner was tested according to CEC-F-02-T-79.

The test for their suitability as dispersants for dirt particles in the engine oil was carried out according to a DKA proposal in a Daimler Benz M 102 E engine.

EXAMPLES

1. Preparation of N-polyisobutyl-β-aminopropionitrile 24 g (0.45 mol) of acrylonitrile were added dropwise in the course of about 30 minutes to 500 g (about 0.5 mol) of a polyisobutylamine prepared according to DE-A1 36 11 230 from a polyisobutene having an average molecular weight of 1,000, dissolved in 500 ml of a $C_{12}$-hydrocarbon mixture, the temperature being kept at 70° C. Stirring was then carried out for three hours at 80° C. The yield was virtually quantitative. The product thus obtained could be directly used for the catalytic hydrogenation.

The product was characterized by the following data: Elemental analysis (Basis for calculation: MW of the starting material polyisobutylamine: 1041):

| Calculated: | C: 83.6% | H: 13.8% | N: 2.6% |
| Found: | C: 83.0% | H: 14.4% | N: 2.2% |

IR spectrum: Band at 2230 $cm^{-1}$ (nitrile band) $^1$H-NMR: 2 triplets at 2.5 and 2.9 ppm, to be assigned to the two $CH_2$ groups in the α- and β-position relative to the nitrile group
¹³C-NMR: Signal at 118.4 ppm (carbon atom of the nitrile group) This shows clearly that the product isolated is N-polyisobutyl-β-aminopropionitrile.

2. Preparation of N-polyisobutyl-1,3-propylenediamine

The reaction mixture from the cyanoethylation (1.) was tranferred to an autoclave, and 5 g of Raney cobalt and 20 g of ammonia were added.

Hydrogenation was carried out for 20 hours at 100° C. and 100 bar. The catalyst was separated off, after which readily volatile components were separated off under reduced pressure from a water pump. 550 g of a virtually colorless, viscous oil having an amine number of 93 (theory: 90–110) were obtained.

3. Engine test results according to CEC-F-02-T-79 Tests as intake system and valve cleaner

| Product | Deposits [mg] Valve No. | | | |
|---|---|---|---|---|
| | 1 | 2 | 3 | 4 |
| Basic value without additives | 530 | 319 | 259 | 651 |
| N-Polyisobutyl-β-aminopropionitrile 400 ppm, according to Example 1 | 41 | 29 | 60 | 5 |
| N-Polyisobutyl-1,3-propylenediamine 400 ppm, according to Example 2 | 2 | 0 | 3 | 0 |

4. Testing of the dispersant effect in the Daimler Benz M 102 E engine

The test fuel used was an unleaded premium grade fuel (RON 95) according to DIN 51,607. The engine oil used was the reference oil RL 136.

Test runs with additive-free gasoline (basic value) and with 250 ppm of test substance and, as comparison, with 250 ppm of polyisobutylamine were carried out.

After the end of the test runs, the engine was dismantled and allowed to drip for 24 hours, after which the rating was carried out. The rating (maximum value 10) of the individual engine parts for the substances from 1. and 2. used as additives is shown in the Tables below:

TABLE 1

Test with N-polyisobutyl-β-aminopropionitrile

| Engine part | Rating | |
|---|---|---|
| | Basic value | 250 mg/kg of N-polyiso-butyl-β-aminopropionitrile |
| Cylinder head cover | 8.7 | 8.4 |
| Oil distribution pipe | 8.3 | 9.0 |
| Cylinder head | 8.3 | 8.9 |
| Oil sump | 9.2 | 9.4 |
| Valve gear cover | 8.5 | 9.2 |
| Mean value | 8.6 | 9.0 |

Through the dispersant effect of aminonitrile, it is possible to increase the mean value in the sludge test in the Mercedes Benz M 102 E engine from 8.6 to 9.0. On the other hand, the use of polyisobutylamine resulted in no improvement compared with the basic value.

TABLE 2

Test with N-polyisobutyl-1,3-propylenediamine

| Engine part | Rating | | Rating |
|---|---|---|---|
| | Basic value | Addition of 250 ppm of diamine from Example 2 | Addition of 250 ppm of polyisobutyl-amine |
| Cylinder head cover | 8.4 | 8.8 | 8.4 |
| Oil distribution pipe | 7.6 | 9.5 | 8.0 |
| Cylinder head | 7.8 | 9.2 | 8.3 |
| Oil sump | 8.9 | 9.5 | 8.9 |
| Valve gear cover | 8.3 | 9.3 | 8.6 |
| Mean value | 8.2 | 9.3 | 8.4 |

The Table shows the better effect of the novel polyisobutylpropylenediamines in comparison with polyisobutylamine. As a result of the dispersant properties of diamine, it is possible to increase the mean value of the rating of the individual engine parts from 8.2 to 9.3. On the other hand, the use of polyisobutylamine resulted only in a slight change to 8.4 compared with the basic value of 8.2.

The results show that the novel substances not only have an excellent effect as intake system and valve cleaners but also exhibit a very good sludge-dispersing effect and are therefore particularly suitable as additives for fuels.

We claim:

1. A β-aminonitrile of the formula I

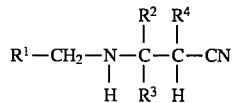

wherein,

R¹ is a polybutyl or polyisobutyl radical having a number average molecular weight of from 500 to 5000 is derived from isobutene and 0–30% by weight of n-butene, and R², R³ and R⁴, independently of one another, are each hydrogen or $C_1$–$C_8$-alkyl, or R² or R⁴ is phenyl.

2. A β-aminonitrile as defined in claim 1, wherein R² and R³ are each hydrogen and R⁴ is methyl.

3. A β-aminonitrile as defined in claim 1, wherein the polybutyl or polyisobutyl radical has a number average molecular weight of from 800 to 1500.

4. A process for the preparation of a β-aminonitrile of the formula I as defined in claim 1, wherein an amine of the formula III

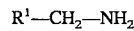

is reacted with a nitrile of the formula IV

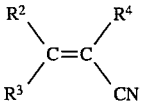

in the presence or absence of a catalyst, R¹ to R⁴ having the meanings stated in claim 1.

5. A lubricant comprising a dispersant-effective amount of a β-aminonitrile of formula I as defined in claim 1.

* * * * *